United States Patent
Sasayama et al.

[11] Patent Number: 6,129,853
[45] Date of Patent: Oct. 10, 2000

[54] BLOOD FILTER SET AND A METHOD OF RECOVERING BLOOD COMPONENTS USING THE SAME

[75] Inventors: Norihisa Sasayama; Toshihiro Kikuchi; Shinichiro Harada; Nobuo Takagi; Takahito Wakabayashi, all of Osaka, Japan

[73] Assignee: Nissho Corporation, Osaka-fu, Japan

[21] Appl. No.: 09/196,760

[22] Filed: Nov. 20, 1998

[30] Foreign Application Priority Data

Nov. 20, 1997 [JP] Japan ................................ 9-320194
Dec. 19, 1997 [JP] Japan ................................ 9-350381
Jun. 19, 1998 [JP] Japan ............................... 10-172805

[51] Int. Cl.[7] .......................... B01D 37/00; A61M 5/165
[52] U.S. Cl. ..................... 210/791; 210/435; 210/503; 210/767; 604/406; 604/408
[58] Field of Search .................. 210/198.1, 232, 210/435, 436, 645, 767, 503, 505, 791; 604/4–6, 403, 406, 408, 409, 410; 436/177, 178

[56] References Cited

U.S. PATENT DOCUMENTS

| | | | |
|---|---|---|---|
| 4,416,777 | 11/1983 | Kuroda et al. | 210/446 |
| 4,466,888 | 8/1984 | Verkaart | 604/406 |
| 4,701,267 | 10/1987 | Watanabe et al. | 210/505 |
| 5,269,924 | 12/1993 | Rochat | 210/445 |
| 5,792,133 | 8/1998 | Rochat | 604/406 |
| 5,858,015 | 1/1999 | Fini | 210/645 |
| 5,935,436 | 8/1999 | Lee et al. | 210/502 |

FOREIGN PATENT DOCUMENTS

| | | |
|---|---|---|
| 0 280 052 A1 | 8/1988 | European Pat. Off. . |
| 0 806 475 A2 | 11/1997 | European Pat. Off. . |
| 4005325 | 2/1991 | Germany ............... 604/408 |

Primary Examiner—Joseph W. Drodge
Attorney, Agent, or Firm—Kubovcik & Kubovcik

[57] ABSTRACT

A filter set for recovering desired blood components from human blood and a method for recovering blood components using the filter set are provided. The filter set includes a bag body and an accommodation vessel for accommodating the bag body therein in a compressed condition. In the method the bag body is provided in the accommodation vessel and is compressed and blood is passed through the compressed bag body. Blood components are adhered to the compressed filter material in the bag body. Thereafter, the compression of the bag body is relieved and a washing solution is passed through the expanded bag body to remove the blood components contained therein.

22 Claims, 11 Drawing Sheets

BLOOD FILTER SET AND A METHOD OF RECOVERING BLOOD COMPONENTS USING THE SAME

FIELD OF THE INVENTION

The present invention relates to a filter set for recovering desired blood components from human blood and a method of recovering blood components using the filter set.

BACKGROUND OF THE INVENTION

It is known that hematopoietic malady occurs as a side effect of chemotherapy for hematopoietic organ tumors such as leukemia, etc., and solid tumors, and bone marrow transplant and peripheral blood stem cell transplant are applied as therapies for the hematopoietic malady. These therapies are methods of recovering from hematopoietic malady, in which hematopoietic stem cells and/or hematopoietic precursor cells contained in bone marrow and peripheral blood are transplanted into the human body. By establishing these transplant therapies, chemotherapy for tumors such as leukemia and solid tumors was made feasible. Further, it was found in recent years that hematopoietic stem cells and/or hematopoietic precursor cells are also contained in umbilical cord blood, and therapy by transplanting hematopoietic cells and/or hematopoietic precursor cells from umbilical cord blood is also expected to be a promising method.

Usually, blood used for these transplant therapies is cryopreserved after collecting until transplanting. If cryopreserved blood is contaminated with erythrocytes, the erythrocytes are lyzed to cause side effects after thawing, therefore, before thawing the blood to be transplanted erythrocytes should be removed from the blood.

Known methods of removing erythrocytes from blood to be transplanted include a centrifugation method and a filter method. The centrifugation method utilizes the difference in specific gravity between erythrocytes and leukocytes derived from hematopoietic stem cells and/or hematopoietic precursor cells. The filter method of recovering leukocytes utilizes a filter for passing erythrocytes but capturing leukocytes derived from hematopoietic stem cells and/or hematopoietic precursor cells and the leukocytes captured therein are recovered with a washing solution.

However, the centrifugation method requires such skills as not to cause disturbance of the interfaces among separated blood components, while the filter method has the disadvantage of low yield because the density of the filter material is so high as to capture hematopoietic stem cell- and/or hematopoietic precursor cell-derived leukocytes at high concentrations, thus making it difficult to remove leukocytes which have adhered to the filter material even if a washing solution is used.

The present invention is directed to solving these problems, and an object of the present invention is to provide a filter set for efficiently recovering desired blood components from blood and a method of recovering blood components by use of the filter set.

As a result of their study for achieving the above object, the present inventors found that desired blood components can be efficiently recovered from blood with a blood filter set which comprises a bag body charged with a filter material and an accommodation vessel for accommodating said bag body. Further, they found that a filter set comprises preferably a bag body consisting essentially of a flexible sheet charged inside with a filter material and a rigid accommodation vessel for accommodating the bag body in a compressed condition or in a freely expansive and compressive condition. Additionally, they found that mainly leukocytes could be efficiently recovered from blood by a bag body charged inside with a filter material and a flexible tube body accommodating the bag body in a compressed condition in the thickness direction.

SUMMARY OF THE INVENTION

That is, the present invention relates to a filter set comprising a bag body having a blood flow inlet and a blood flow outlet and charged with a filter material, and an accommodation vessel for accommodating said bag body.

One embodiment of the present invention is a filter set comprising a bag body having a blood flow inlet and a blood flow outlet and consisting of a flexible sheet charged inside with a filter material, and a rigid accommodation vessel for accommodating said bag body which is freely removable therefrom and for accommodating said bag body in a compressed condition at the time of accommodation.

The rigid accommodation vessel is not particularly limited and includes a rectangular parallelepiped vessel provided with a takeout port from which the bag body can be removed or a vessel provided with a lid which can be opened and closed or the like.

Another embodiment of this invention is a filter set comprising a bag body having a blood flow inlet and a blood flow outlet and consisting of a flexible sheet charged inside with a filter material, and a rigid accommodation vessel for accommodating said bag body, wherein said bag body is compressed by filling the vessel with compressed gas, and after blood is passed through said bag body in a compressed condition, the compressed gas is exhausted to relieve the compression of said bag body through which a washing solution is then passed.

The rigid accommodation vessel includes a vessel which compresses said bag body by filling with compressed gas and relieves the compression of the bag body by exhausting the compressed gas. Also, the vessel is capable of further expanding the bag body by evacuating the inside of the vessel after relieving the compression condition.

Another embodiment is a filter set comprising a bag body having a blood flow inlet and a blood flow outlet and being charged inside with a filter material and a flexible tube body accommodating the bag body in a compressed condition in the thickness direction, wherein said bag body can be removed from said tube body.

The tube body is a heat-shrinkable tube or possesses a similar length to that of the bag body and a smaller volume than that of the bag body prior to compression of the bag body. If the tube body is heat-shrinkable, the tube body is preferably provided with a rupturable portion. And if the tube body possesses a similar length to that of the bag body and a smaller volume than that of the bag body, the tube body is preferably provided at at least one end with a grasping portion for removing the tube body from the bag body.

The present invention relates to a method of recovering blood components comprising accommodating a bag body into an accommodation vessel, wherein the bag body has a blood flow inlet and a blood flow outlet and has a filter material charged therein, compressing the bag body by the accommodation vessel, passing blood through the bag body in a condition compressed by said accommodation vessel to cause adherence of blood components to the filter material, removing the bag body from the accommodation vessel and expanding the bag body, passing a washing solution through the inside of the bag body in an expanded condition so as to wash off the blood components adhered to the filter material, and recovering the blood components.

One embodiment of the present invention relates to a method of recovering blood components comprising filling an accommodating vessel containing a bag body with compressed gas to compress the bag body, wherein the bag body has a blood flow inlet and a blood flow outlet, is made of a flexible sheet and is charged inside with a filter material, passing blood through the bag body in a compressed condition to cause blood components to adhere to the filter material, exhausting the compressed gas to relieve the compression condition of the bag body, passing a washing solution through the inside of the bag body so as to wash off the blood components adhered to the filter material and recovering the blood components.

After the compressed gas is exhausted, the inside of the vessel may be evacuated to cause said bag body to further expand and then the washing solution is passed through the bag body to wash and recover blood components that have adhered to said filter.

Another embodiment is a method of recovering blood components comprising providing a bag body accommodated in a flexible tubular bady in a compressed condition in a thickness direction, passing blood through the bag body, wherein the bag body has a blood flow inlet and a blood flow outlet, and is made of a flexible sheet charged therein with a filter material, removing the bag body from the flexible tubular body to relieve the compression of the bag body, passing a washing solution through the inside of the bag body so as to wash off the blood components adhered to the filter material, and recovering the blood components.

DESCRIPTION OF THE PREFERRED EMBODIMENTS

Examples of the present invention are described below with reference to the drawings.

Figure 1:
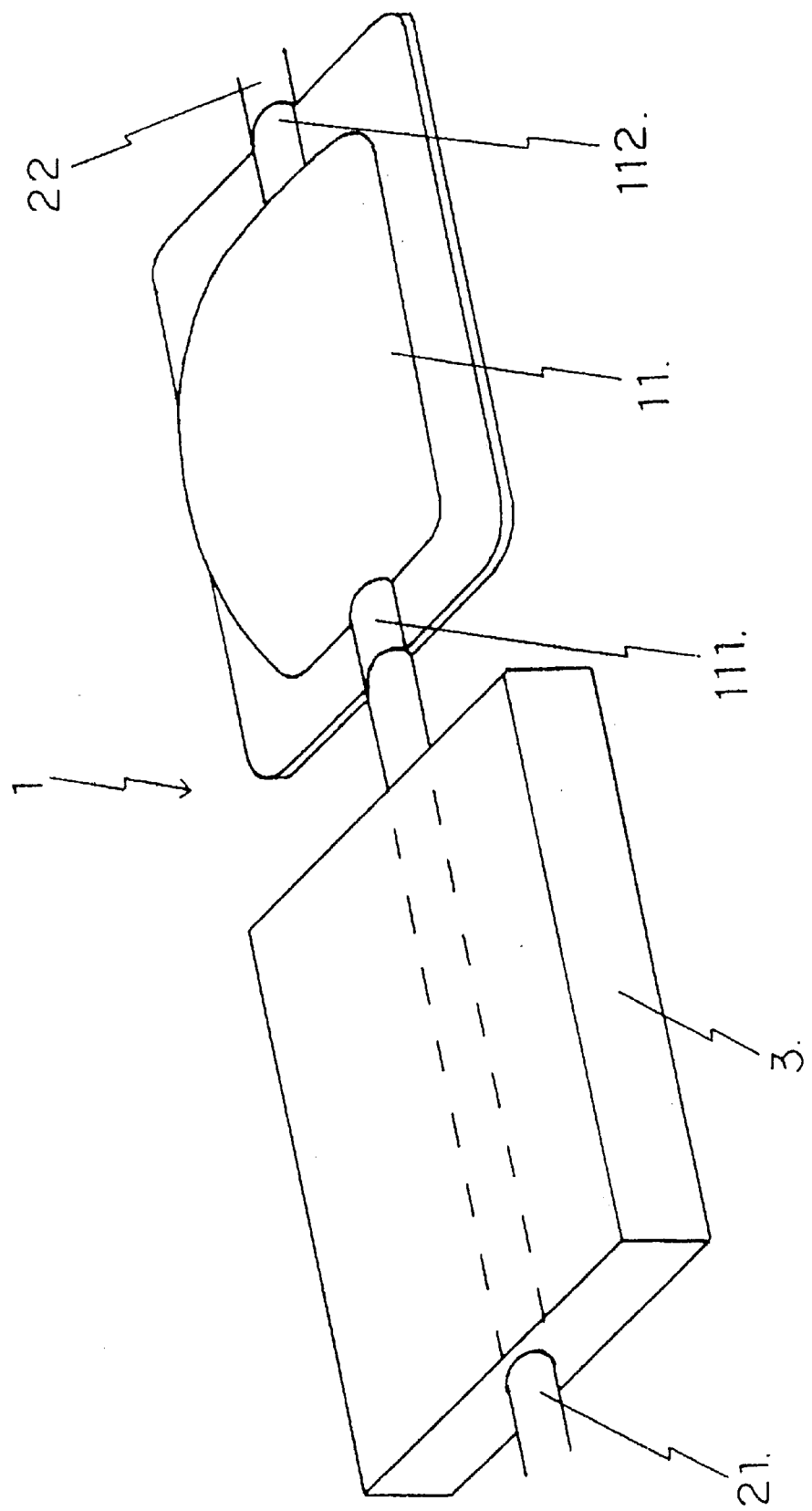
FIG. 1 is a drawing showing one embodiment of the filter set of the present invention.
Figure 2:
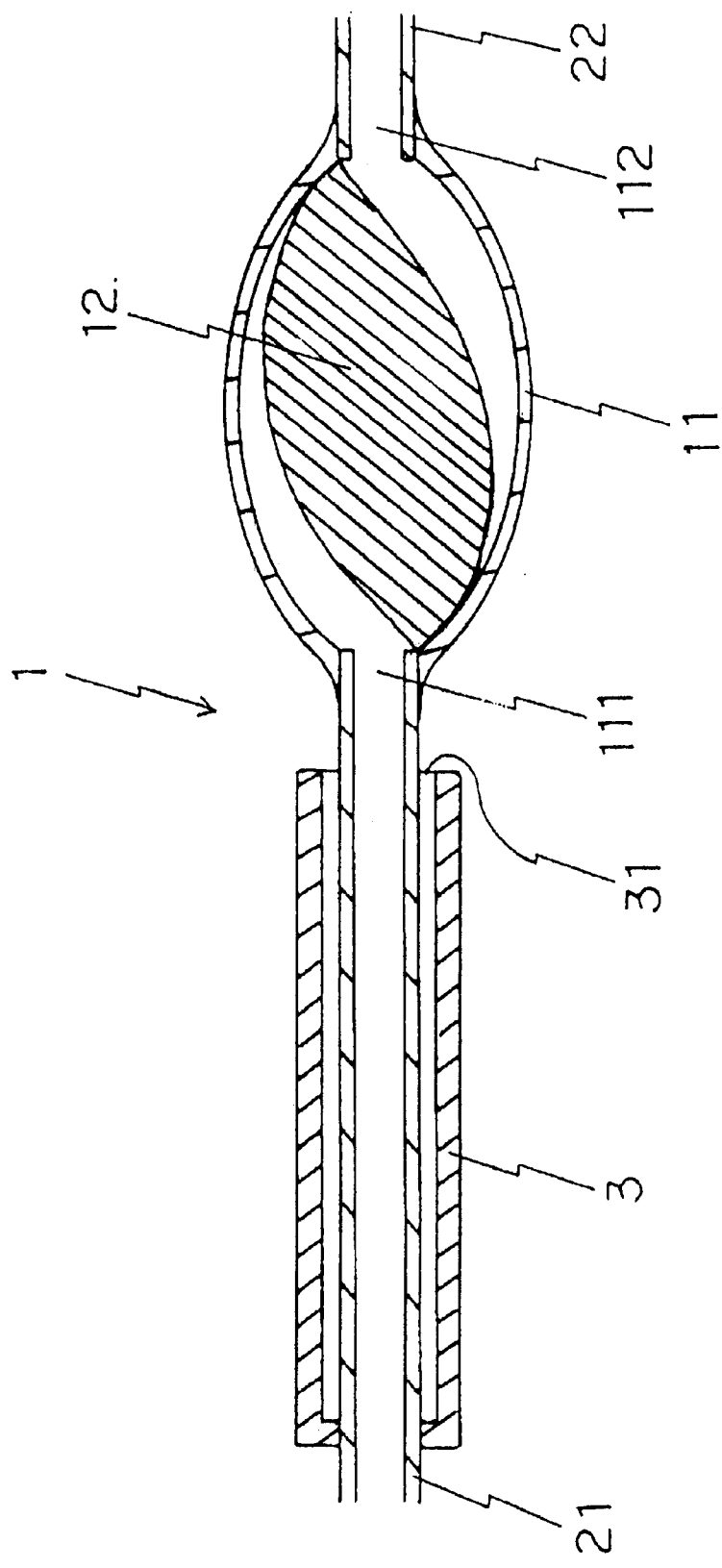
FIG. 2 is a longitudinal section of the filter set shown in FIG. 1.
Figure 3:
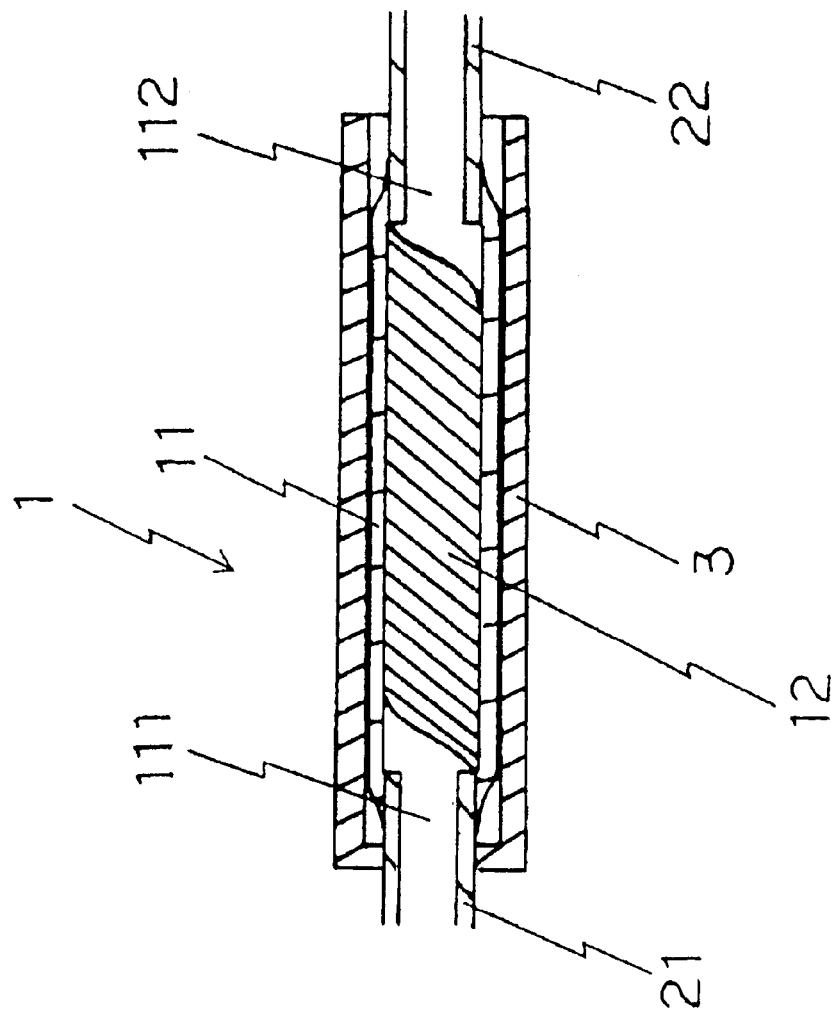
FIG. 3 is a drawing further illustrating the filter set shown in FIG. 1.

As shown in FIGS. 1, 2 and 3, the filter set 1 is composed of bag body 11 charged inside with filter material 12, tube 21 connected to blood flow inlet 111 and tube 22 connected to blood flow outlet 112 of the bag body 11, and an accommodation vessel 3 for accommodating the bag body 11 in a compressed condition. FIGS. 1 and 2 show the bag body 11 removed from the accommodation vessel 3 and FIG. 3 shows the bag body 11 accommodated in the accommodation vessel 3.

The bag body 11 consists of two flexible sheets welded along the edge thereof. The material of the bag body 11 is not particularly limited and includes soft polyvinyl chloride, ethylene-vinyl acetate copolymers, styrene-butadiene-styrene copolymers, polyurethane, polyamide, polyester, polyethylene, polypropylene etc. The welding method is preferably thermal welding, high frequency welding, ultrasonic welding, solvent welding or the like.

The bag body 11 is charged inside with the filter material 12, and the filter material 12 is sealed along the edge to the weld of the bag body 11.

The filter material 12 is selected from materials having an ability to capture desired blood components (mainly leukocytes) from blood. The filter material is typically a fibrous material including, for example, filaments, slivers and long staple fibers. Both organic and inorganic fibers can be used. The organic fibers include synthetic fibers such as polyester, polypropylene, polyethylene, polymethyl methacrylate, polyamide and the like, and natural fibers such as cellulose, regenerated cellulose, cotton and the like. Inorganic fibers include, for example, glass fibers. The fibrous filter material maybe in the form of fibers, aggregates thereof and woven and non-woven fabrics. A preferred fibrous filter comprises cellulose or a regenerated cellulose fiber aggregate.

The diameter of the fibers is preferably in the range of 0.1 to 40 $\mu$m, preferably 0.5 to 25 $\mu$m, more preferably 0.5 to 10 $\mu$m, and most preferably 0.5 to 3 $\mu$m. In the case of a diameter of less than 0.1 $\mu$m, spaces between the fibers per unit area tend to become small thus increasing filtration resistance, while in the case of a diameter of more than 40 $\mu$m, the volume of the fibers tends to become large thus increasing absorption of undesired blood components.

The bulk density of the filter material in compressed bag body 11 is 0.05 to 0.50 g/cm$^3$, preferably 0.08 to 0.30 g/cm$^3$, and more preferably 0.10 to 0.20 g/cm$^3$. If the bulk density is less than 0.05 g/cm$^3$, the yield of leukocytes recovered in the filter tends to decrease, and if the bulk density exceeds 0.50 g/cm$^3$, the flow rate of blood passing through the filter tends to decrease.

The amount of the filter material 12 charged can be readily determined by one skilled in the art and may be any amount sufficient to achieve degrees of capture possessed by a conventional leukocyte-removing filter in a compressed condition.

The filter material 12 may be formed of two or more materials or may comprise layers of different substances laminated therein. If the filter material 12 is composed of a multi-layer fiber agglomerate, at least one layer has a fiber diameter of 25 $\mu$m or less and a bulk density of 0.05 to 0.50 g/cm$^3$ in a compressed condition. The multi-layer structure is composed of 2 to 6 layers, where a layer near the blood flow inlet consisting of fiber agglomerate having a large fiber diameter and a high bulk density and a layer near the blood flow outlet consisting of a fiber agglomerate having a small fiber diameter and a low bulk density are preferably arranged so that leukocytes can be captured in the order of a decreasing diameter through the layers.

For example, if the filter material 12 in compressed bag body 11 is a multi-layer fiber agglomerate consisting of a fiber agglomerate with a fiber diameter of 10 μm and a bulk density of 0.23 g/cm$^3$ as a first layer, a fiber agglomerate with a fiber diameter of 3.5 μm and a bulk density of 0.11 g/cm$^3$ as a second layer and a fiber agglomerate with a fiber diameter of 1.8 μm and a bulk density of 0.12 g/cm$^3$ as a third layer, then blood components with large diameters will be captured by the first layer, monocytes and granulocytes by the second layer and lymphocytes by the third layer.

Further, the filter material 12 is not limited to the structure in which it is sealed along the edge to the weld of the bag body 11, and as shown in, e.g., Japanese Laid-Open Patent Publication No.67952/1995, the filter material may be formed into a hanging-bell form, and its edge is sealed by welding from a lower part to the side while an upper part is open and the end of the upper part is welded with a bag body.

In the bag body 11, the blood flow inlet 111 and the blood flow outlet 112 are arranged opposite each other relative to the filter material 12, and blood introduced from the blood flow inlet 111 is passed through the filter material 12 and discharged from the blood flow outlet 112. Similarly, a washing solution introduced from the blood flow inlet 111 or the blood flow outlet 112 is passed through the filter material 12 and discharged from the blood flow outlet 112 or the blood flow inlet 111. The bag body 11 made of a flexible sheet charged with the filter material 12 is freely expansive and compressive, and spaces between the fibers in the filter material 12 are variable. Therefore, spaces between the fibers are made small when blood is passed, while spaces between the fibers is made large when a washing solution is passed. Here, the function of the washing solution is to wash away the blood components having adhered to filter material 12 and recover them. The washing solution is preferably physiological saline, Hank's solution, Dulbecco phosphate buffer, dextran, etc. which may optionally contain human serum albumin or an anti-coagulation agent.

Tube 21 is connected to the blood flow inlet 111, and tube 22 is connected to the blood flow outlet 112. The connection method includes welding, adhesion, connection by a connector, etc. In the case of connection by a connector, usually the tube 21 has been previously connected to the bag body 11, but the tube 21 may be aseptically connected to the bag body 11 just before use. When the filter set of the present invention is used, one end of each of tubes 21 and 22 is attached to the bag body 11, and a blood bag (not shown) is attached to the other end of each of tubes 21 and 22, but in place of tubes 21 and 22, syringes etc. may be connected to the blood flow inlet 111 and the blood flow outlet 112.

The accommodation vessel 3 is typically a rectangular parallelepiped vessel which is formed of a rigid material so as to accommodate the bag body 11 in a compressed condition and which is provided with a bag body-removing port 31 from which the bag body 11 can be removed. The vessel is attached so as to slide freely in the longitudinal direction on tube 21 attached to the side of the blood flow inlet 111. The material of the vessel includes synthetic resins such as polycarbonate, polystyrene, rigid polyvinyl chloride, polypropylene, etc. or metals. The accommodation vessel 3 preferably has a size sufficient to compress the bag body 11 to achieve degrees of capture possessed by a conventional leukocyte-removing filter. However, the accommodation vessel 3 in the present invention is not limited to the shape shown in FIGS. 1, 2 and 3, and the accommodation vessel 3 may have any shape by which the bag body 11 is accommodated in a compressed condition so as to capture desired blood components in the filter material 12 and from which the bag body 11 can be removed so as to efficiently recover blood components captured in the filter material 12.

Figure 4:
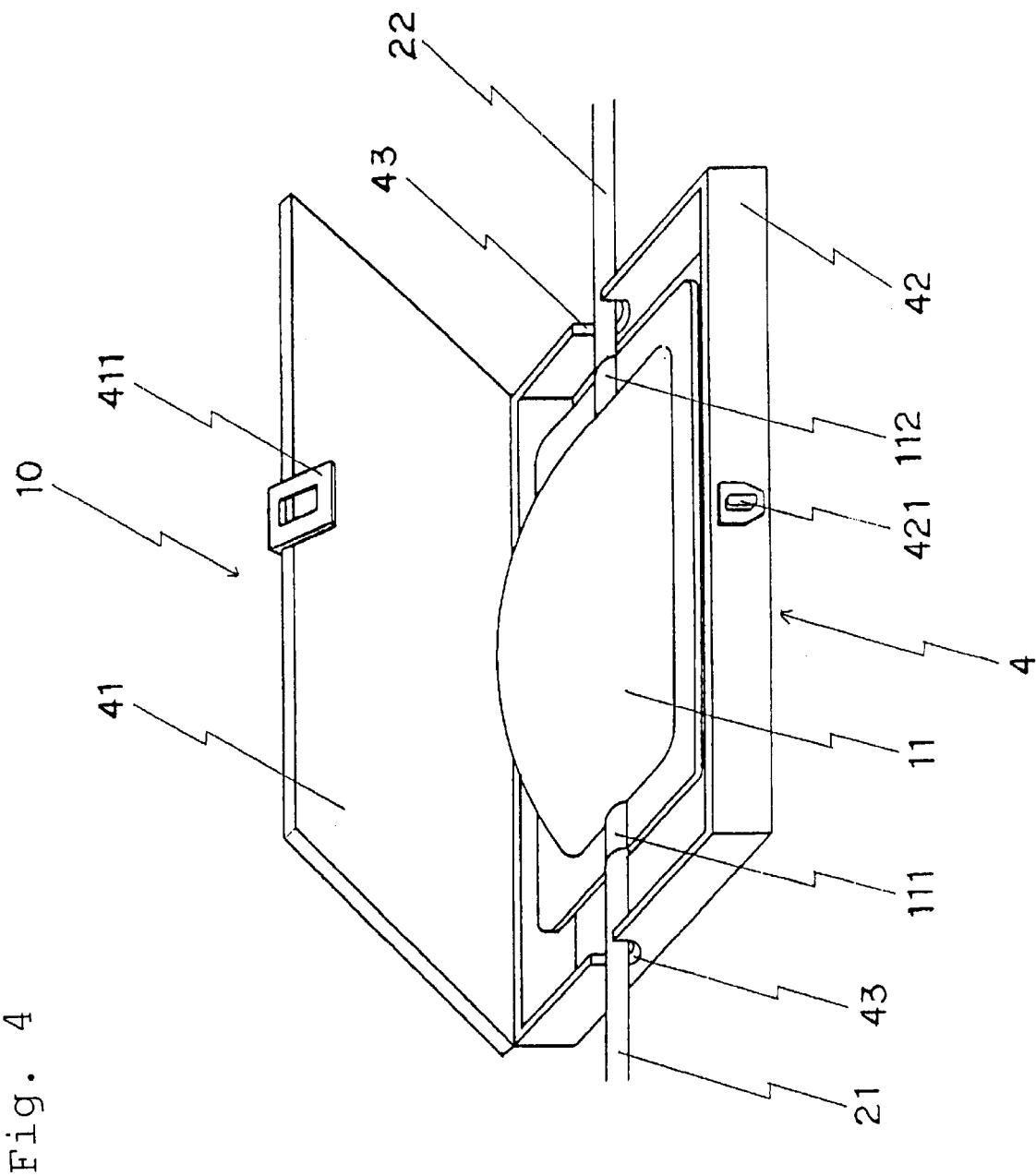
FIG. 4 is a drawing showing another embodiment of the filter set of the present invention.

The filter set of the present invention may be constituted as shown in FIG. 4. The accommodation vessel 4 has a lid 41, which can be opened and closed freely, the bag body accommodated therein is compressed by closing the lid 41 in FIG. 4. A groove 43 in which a tube connected with a bag body 11 is inserted and a connecting means to close lid 41 are provided on the accommodation vessel 4. The connecting means may be such that the connection cannot be disconnected by the resiliency of the compressed bag body when the lid is closed. For instance, the connection means is constituted by an arm 411 provided on the lid 41 and a protuberance 421 connected with said arm 411 and provided on the vessel body 42. In this example this filter set has advantages that there is no risk of damaging the bag body 11 and it may be possible to relieve a compression of the bag body 11 more rapidly because it is not necessary to touch the bag body directly. The lid of the accommodation vessel is simply opened.

The method of recovering hematopoietic stem cell- and/or hematopoietic precursor cell-derived leukocytes from umbilical cord blood by using filter set 1 shown in FIGS. 1, 2 and 3 will now be described.

First, the bag body 11 is accommodated in the accommodation vessel 3, and umbilical cord blood is passed from the blood flow inlet 111, through the bag body 11 in a compressed condition, to the blood flow outlet 112. In this step, the filter material 12 is compressed and spaces between the fibers are made small, so leukocytes derived from hematopoietic stem cells and/or hematopoietic precursor cells can be efficiently captured.

Then, the bag body 11 is removed from the accommodation vessel 3, and a washing solution is passed from the blood flow outlet 112 to the blood flow inlet 111. In this step, the compression of the filter material 12 is relieved and spaces between the fibers are increased, so hematopoietic stem cell- and/or hematopoietic precursor cell-derived leukocytes adhered to the filter material 12 can be easily removed and easily washed away with the washing solution for recovery. Because spaces between the fibers are increased, the washing solution can be easily passed therethrough to reduce the time necessary for passing the solution. Here, the washing solution may be introduced from the blood flow inlet 111 or blood flow outlet 112.

The washing solution containing leukocytes derived from hematopoietic stem cells and/or hematopoietic precursor cells is recovered in a vessel and then subjected to separation by centrifugation or passage through a filter, whereby hematopoietic stem cells and/or hematopoietic precursor cells are recovered. At this step, a filter that captures granulocytes and monocytes but passes hematopoietic stem cells and/or hematopoietic precursor cells is preferably used.

The blood filter set of the present invention is now described with reference to FIGS. 6, 7 and 8. The blood filter set 1 is composed of the bag body 11 charged inside with the filter material 12, tube 21 connected to blood flow inlet 111 and tube 22 connected to blood flow outlet 112 for the bag body 11, and the rigid accommodation vessel 3 for accommodating the bag body 11. The accommodation vessel 3 includes ports 31, 32 provided on regions where tubes 21, 22 connected to the bag body 11 penetrate the accommodation vessel 3, in order to maintain the airtightness of the vessel. Introduction and discharge of gas is conducted through a 2-directional stopcock 33.

The accommodation vessel 3 is a rectangular parallelepiped vessel which is formed of a rigid material so as to accommodate the bag body 11 in a compressed condition by filling the vessel with compressed gas and which is provided with ports 31, 32 for maintaining the airtightness of the tube-connecting portions and with the 2-directional stopcock 33 for introducing and discharging gas. O-rings (not shown) are inserted between ports 31, 32 and tubes 21, 22 to maintain the airtightness of the accommodation vessel 3. If the accommodation vessel 3 is formed of synthetic resin, the ports and the tubes may be welded by ultrasonic wave. The compressed gas used includes inert gases such as air, nitrogen, argon, etc.

Because the bag body 11 is compressed to achieve degrees of capture possessed by a conventional leukocyte-removing filter; the accommodation vessel 3 should be formed of a material capable of withstanding the compression. The material includes synthetic resins such as polycarbonate, polystyrene, rigid polyvinyl chloride, etc. and metals such as stainless steel, aluminum, etc. The accommodation vessel 3 is preferably of such a size that it can accommodate the bag body 11 when the bag body is expanded to increase spaces between the fibers in the filter material 12.

However, the accommodation vessel 3 in the present invention is not limited to the shape shown in the drawings and can have any shape by which the bag body 11 can be accommodated in a compressed condition so as to capture desired blood components and by which the bag body 11 can be expanded so as to efficiently recover blood components captured in the filter material 12.

Figure 5:
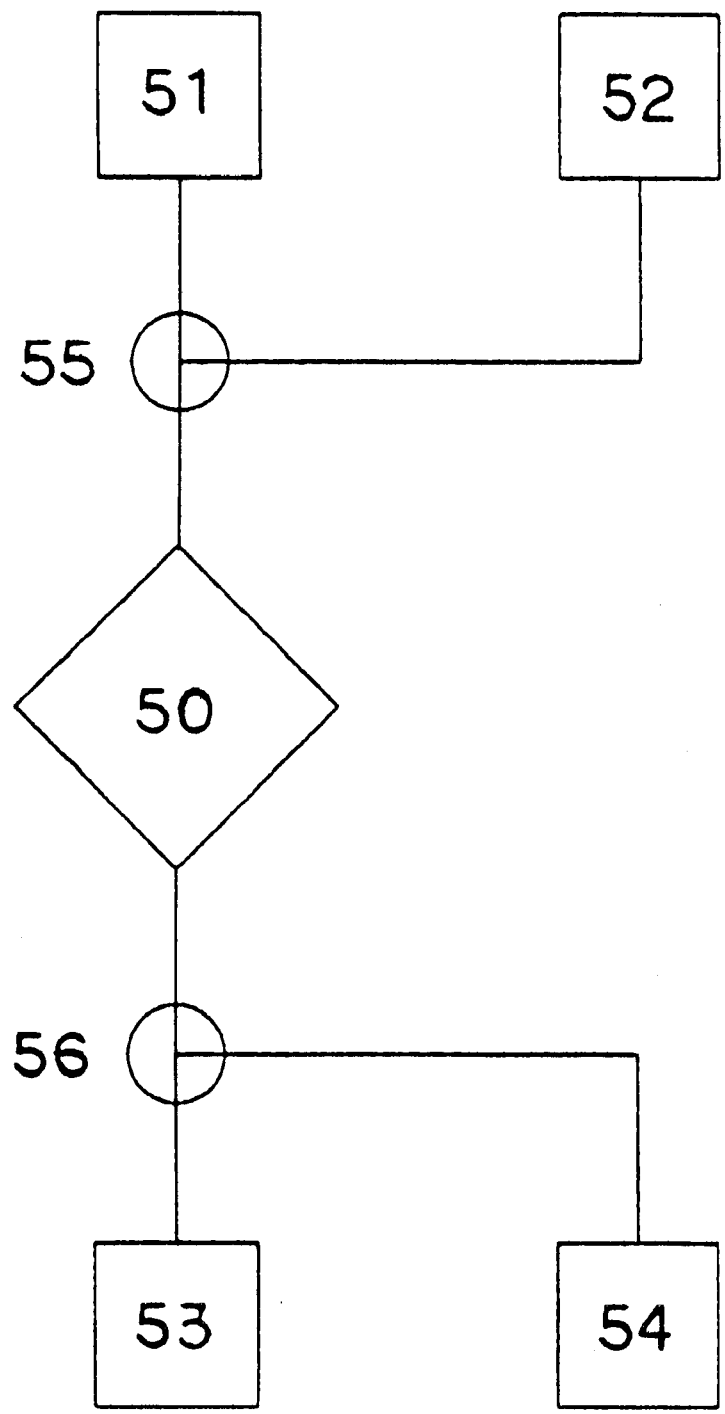
FIG. 5 is a drawing illustrating the method of recovering blood components according to the present invention.
Figure 6:
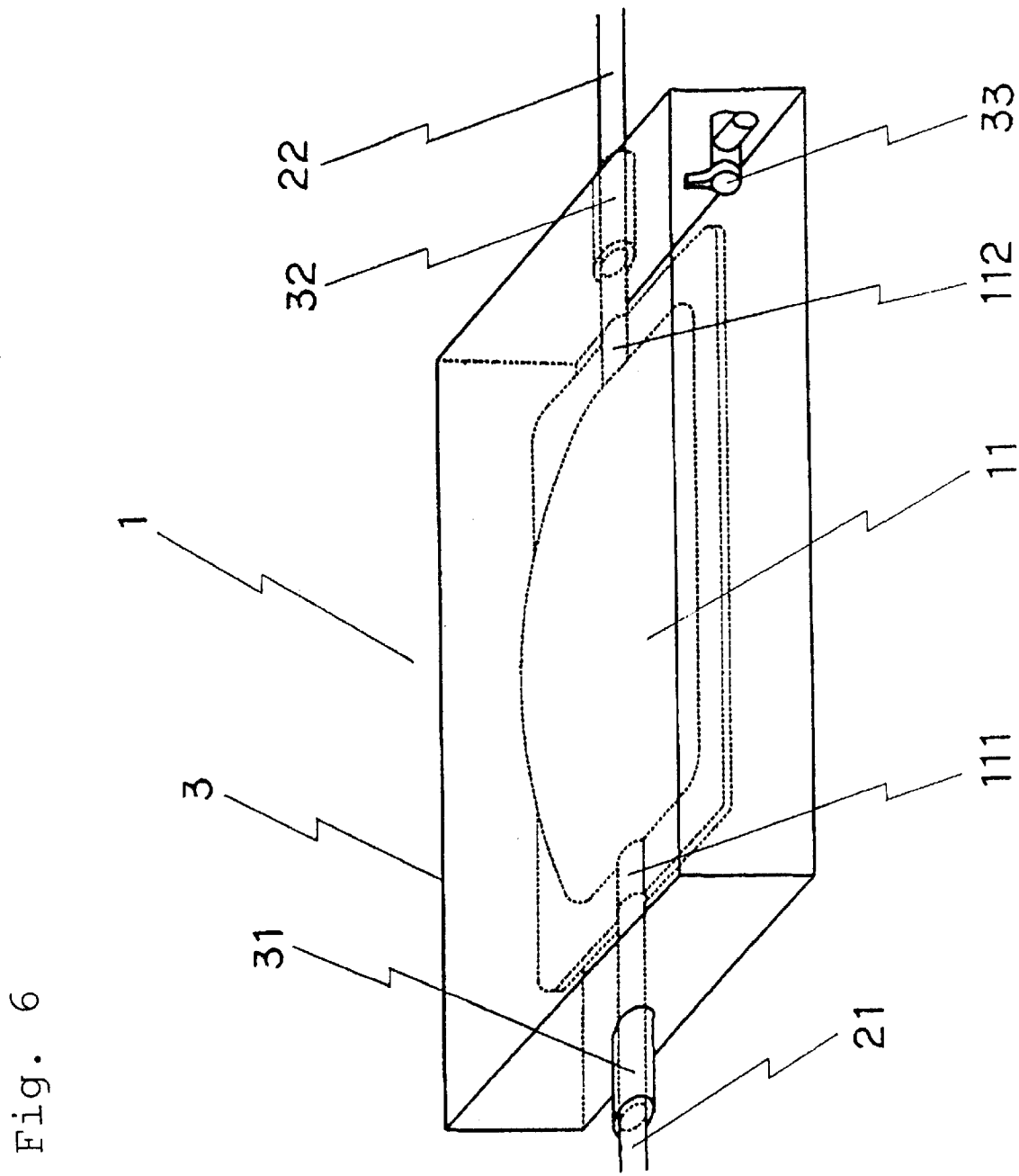
FIG. 6 is a drawing showing another embodiment of the blood filter set of the present invention.

FIG. 5 is a drawing illustrating a the method of collecting blood components by the use of the blood filter set in FIG. 6. Blood components collecting apparatus 50 in FIG. 5 includes a filter set of this invention.

From the blood bag 51 in which whole blood was accommodated, the whole blood is passed through a 3-directional stopcock 55, then through tube 21, and is introduced from the blood flow inlet 111 into the inside of the bag body 11 which is in a compressed condition. Leukocytes are captured in the filter material 12, for example, in spaces between the fibers therein, while erythrocytes are passed through the filter material 12, then through the blood flow outlet 112, tube 22 and 3-directional stopcock 56 and are recovered in the erythrocyte-recovery bag 53. The erythrocyte-recovery bag 53 can also accommodate platelets in addition to erythrocytes, depending on the type of the filter material 12. Thereafter, a washing solution in the wash bag 52 is passed through the 3-directional stopcock 55, tube 21, and blood flow inlet 111, thus washing away leukocytes from the filter material 12 in which spaces between the fibers have been increased, whereby the leukocytes are passed through the blood flow outlet 112, tube 22, and 3-directional stopcock 56 and recovered in the leukocyte-recovery bag 54.

The method of recovering hematopoietic stem cell- and/or hematopoietic precursor cell-derived leukocytes from umbilical cord blood by the use of the filter set 1 in FIG. 6 is now described.

First, umbilical cord blood is passed from the blood flow inlet 111, through the bag body 11 compressed in the accommodation vessel 3 by filling the vessel with compressed gas, to the blood flow outlet 112. In this step, the filter material 12 is compressed, and leukocytes derived from hematopoietic stem cells and/or hematopoietic precursor cells are captured in spaces between the fibers. The compressed gas may be supplied by a pump or may be injected by a syringe that is directly connected to the 2-directional stopcock 33.

Then, the 2-directional stopcock 33 is opened, and the compressed gas is exhausted from the accommodation vessel 3 to relieve the compressed condition of the bag body 11, thus expanding the bag body 11. Washing solution is then passed from the blood flow inlet 111 through the bag body 11 to blood flow outlet 112. During this step, the compression of the filter material 12 is also relieved and spaces between the fibers are made large, so leukocytes derived from hematopoietic stem cells and/or hematopoietic precursor cells that have adhered to the filter material 12 are easily removed, easily washed away with the washing solution, and recovered in the leukocyte-recovery bag 54 in FIG. 6. Here, the washing solution may be introduced from the blood flow inlet 111 or blood flow outlet 112.

The washing solution containing leukocytes derived from hematopoietic stem cells and/or hematopoietic precursor cells is recovered in a blood-recovery vessel and then subjected to separation by centrifugation or passage through a filter, whereby hematopoietic stem cells and/or hematopoietic precursor cells are recovered. As the filter used, a filter which captures granulocytes and monocytes but passes hematopoietic stem cells and/or hematopoietic precursor cells is preferably used.

In this case, the inside of the vessel may be further evacuated by exhausting the compressed gas followed by evacuation by a vacuum pump, or by reducing the pressure in the vessel by use of the syringe connected to the 2-directional stopcock 33, whereby the bag body 11 is further expanded and spaces between the fibers in the filter are further enlarged thus facilitating recovery and reducing the time required for recovery.

As described above, because the filter set of the present invention can relieve the compressed condition by merely opening the 2-directional stopcock 33, its operation is easier than in the prior art. Further, the washing solution can be easily passed through the filter by increasing spaces between the fibers to reduce the time necessary for passing the solution.

Figure 9:
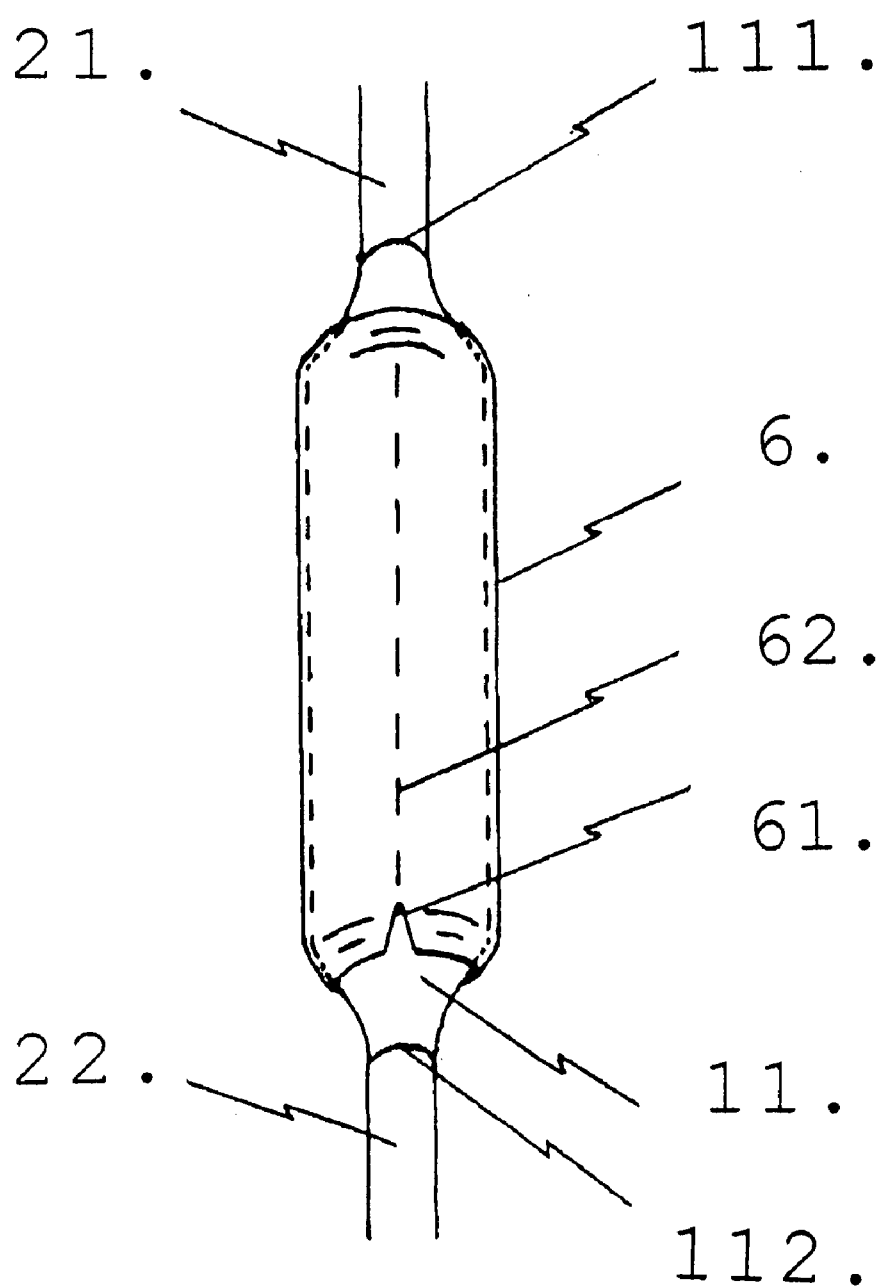
FIG. 9 shows a further embodiment of the filter set of the present invention.
Figure 10:
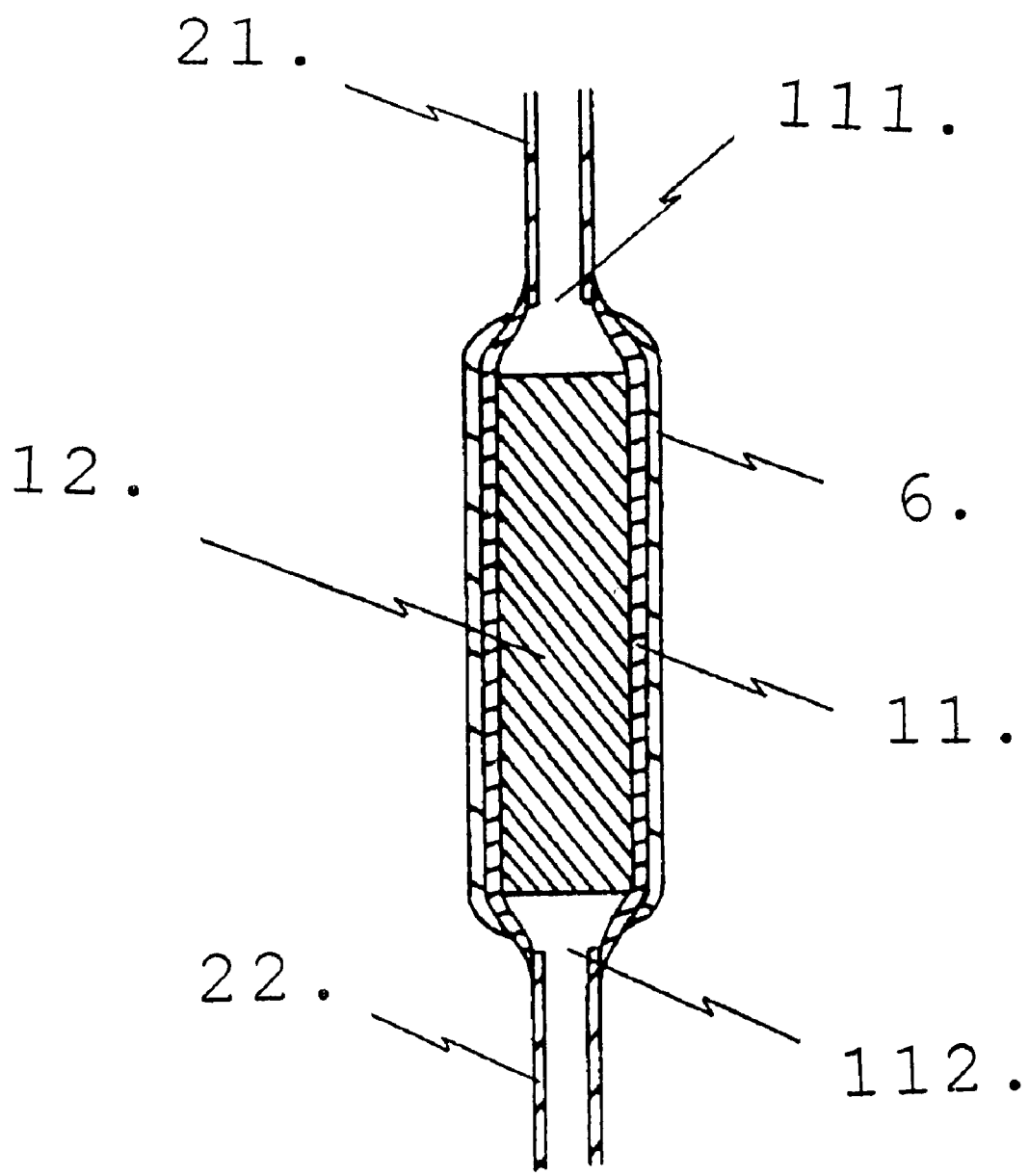
FIG. 10 is a longitudinal section of the filter set shown in FIG. 9.
Figure 11:
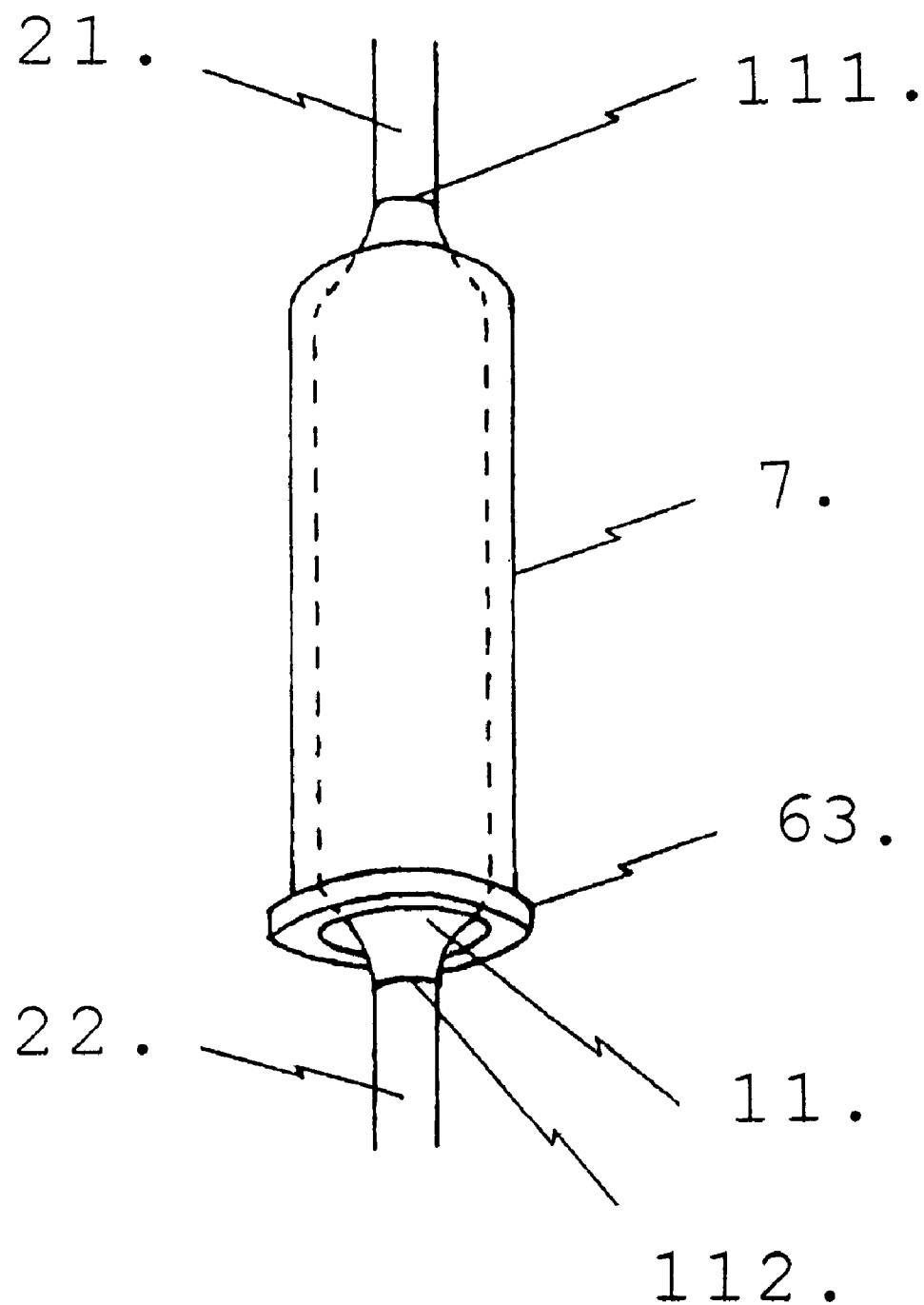
FIG. 11 shows another embodiment of the filter set of the present invention.

As shown in FIGS. 9, 10 and 11, another embodiment of the filter set is composed of bag body 11 charged inside with filter material 12, tube 21 connected to blood flow inlet 111 and tube 22 connected to blood flow outlet 112 for the bag body 11, and a flexible tube body 6 (FIG. 9) or 7 (FIG. 11) for accommodating the bag body 11 in a compressed state in the thickness direction.

The bag body 11 consists of two flexible sheets which were welded along the edge thereof by thermal welding, high-frequency welding, ultrasonic welding, solvent welding or the like. The material of the bag body 11 is preferably synthetic resin such as soft polyvinyl chloride, ethylene-vinyl acetate copolymers, styrene-butadiene-styrene copolymers, polyurethane, polyamide, polyester, polyethylene, polypropylene, etc.

As shown in FIG. 10, the bag body 11 is charged inside with filter material 12. The filter material 12 is to capture mainly leukocytes from blood, and it is composed preferably of synthetic fibers such as polyester, polypropylene, polyethylene, polymethyl methacrylate, polyamide, etc., and natural fibers such as cotton, etc. The diameter of the fibers is preferably in the range of 0.1 to 40 $\mu$m. In the case of a diameter of less than 0.1 $\mu$m, spaces between the fibers per unit area tend to become small thus increasing filtration resistance, while in the case of a diameter of more than 40 $\mu$m, the volume of the fibers tends to become large thus increasing absorption of excess blood components. The amount of the filter material 12 charged may be any amount that is sufficient to achieve degrees of capture possessed by a conventional leukocyte-removing filter when the filter material 12 is in a compressed condition.

The tube body 6 shown in FIG. 9 consists of a heat-shrinkable tube formed of one or more layers of synthetic resin such as polyvinyl chloride, polyester, polypropylene, polyethylene, polystyrene etc., and after the bag body 11 is accommodated therein, the tube body 3 is heat-shrunk to compress the bag body 11 to a desired shrinkage condition. The tube body 6 may be provided at one end (in the side of tube 22) with a ruptured portion such as V-shaped cutting 61, and a perforation may be provided along the longitudinal direction from the cutting 61 so that after blood is passed through the bag body 11, the tube body 6 can be easily ruptured a long the perforation 62. The thickness of tube body 6 is not particularly limited, but is usually formed to have a thickness of about 10 to 100 $\mu$m.

As shown in FIG. 11, a tube body 7 possessing a similar length to that of the bag body 1 and a smaller volume than that of the bag body 11 can be used to accommodate the bag body 11 in a desired compressed condition. The tube body 7 may be provided at one end (on the side of tube 22) with a grasping portion 63 for removing the tube body 7 from the bag body 11. After blood is passed through the bag body 11, the tube body 7 easily slides so that it can be removed from the bag body 11. That is, it can easily slide for removal from the bag body 11 by supporting the bag body 11 with one hand and pulling the grasping portion 63 with the other hand. The material of the tube body 7 is preferably synthetic resin such as polyvinyl chloride, polyethylene, polypropylene, etc. The grasping portion 63 may be formed of synthetic resin such as polypropylene, polyethylene, etc., but the grasping portion 63, if provided in a rib form along the edge of the tube body 7 as shown in this example, is formed preferably into one body using the same material as the tube body 7.

The tube body may have any shape that can compress the bag body 11 to achieve degrees of capture possessed by a conventional leukocyte-removing filter, and the shape is not limited to the shapes shown in FIGS. 9 and 11.

A method of recovering hematopoietic stem cell- and/or hematopoietic precursor cell-derived leukocytes from umbilical cord blood is described with reference to FIG. 9.

First, umbilical cord blood is passed from the blood flow inlet 111, through the bag body 11 accommodated in the tube body 6, to the blood flow outlet 112. In this step, the filter material 12 is compressed so as to attain suitable spaces between the fibers and, therefore, leukocytes derived from hematopoietic stem cells and/or hematopoietic precursor cells can be accurately captured.

Then, the tube body 6 is ruptured along the perforation 62 from the ruptured portion 61 to remove the bag body 11 from the tube body 6, and a washing solution is passed from the blood flow outlet 112 to the blood flow inlet 111. During this step, the compression of the filter material 12 is relieved and spaces between the fibers are increased. Therefore, leukocytes derived from hematopoietic stem cells and/or hematopoietic precursor cells that have adhered to the filter material 11 are easily removed and easily washed away with the washing solution for recovery. Because spaces between the fibers are made large, the washing solution can be easily passed therethrough to reduce the time necessary for passing the solution. Here, the washing solution may be introduced from the blood flow inlet 111 or blood flow outlet 112.

EXAMPLE 1

The filter set 1 shown in FIG. 1 was used. The filter material 12 charged in the bag body 11 consists of a 3-layer nonwoven fabric (filtration area 12.6 cm$^2$) using polyethylene terephthalate fibers. The structure of the three layers in the bag body 11 when compressed in the accommodation vessel 3 consists of a nonwoven fabric with a fiber diameter of 10 $\mu$m and a bulk density of 0.23 g/cm$^3$ in an upper layer as a first layer, a nonwoven fabric with a fiber diameter of 3.5 $\mu$m and a bulk density of 0.09 g/cm$^3$ in an interlayer as a second layer and a nonwoven fabric with a fiber diameter of 1.8 $\mu$m and a bulk density of 0.12 g/cm$^3$ in a sublayer as a third layer. The weight_ratio thereof was 52:21:27, and the total thickness was 7.4 mm.

As show n in FIG. 3, the bag body 11 was accommodated in the accommodation vessel in a compressed condition and 100 ml bovine blood containing ACD solution as an anti-coagulation agent was passed therethrough at a flow rate of 5 ml/min. whereby leukocytes were captured in the inside of the bag body 11 while erythrocytes were passed through the bag body 11 and recovered in the erythrocyte-recovery bag 53 shown in FIG. 5.

The yield of erythrocytes recovered in the erythrocyte-recovery bag 53 was 92%, and the yield of platelets therein was 15%.

Then, the 3-directional stopcock 56 was closed and then the accommodation vessel was removed as shown in FIG. 1 and the compressed condition of the bag body 11 was relieved. After the bag body 11 was filled with dextran to widen the spaces between the fibers, 150 ml of a dextran solution was poured out at a flow rate of 15 ml/min. and accommodated into the leukocyte accommodation bag 54. The ratio of enlargement of the filter material 12 due to removing of the bag body 11 from the accommodation vessel 3 and the recovery of leukocytes recovered_in the leukocyte-recovery bag 54 are shown in Table 1.

The volume expansion ratio is the ratio of the inner volume of the bag body 11 in which the compression of the filter material 12 was relieved by removing the accommodation vessel versus the inner volume of the bag body 11 in which the filter material 12 was compressed by accommodating the bag body in the accommodation vessel. The leukocyte recovery ratio is the ratio of the number of leukocytes in the dextran solution recovered in the leukocyte-recovery bag 54 versus the number of leukocytes in blood initially accommodated in the blood bag 51.

EXAMPLE 2

The filter set 1 shown in FIG. 1 is used. A nonwoven fabric with a fiber diameter of 10 $\mu$m and a nonwoven fabric with a fiber diameter of 1.83 $\mu$m were immersed in 0.25% 2-hydroxyethyl methacrylate/diethylaminoethyl methacrylate copolymer in ethanol to make a 2-layer laminate. A filter material 12 having a 2-layer structure consisting of said nonwoven fabric having a fiber diameter of 10 $\mu$m and a bulk density of 0.32 g/cm$^3$ as an upper layer (first layer) and said nonwoven fabric with a fiber diameter of 1.83 $\mu$m and a bulk density of 0.12 g/cm$^3$ as a sublayer (second layer) when in a compressed condition (volume ratio 72.7:27.3) was accommodated in a bag body 11 (filtration area 12.6 cm$^2$)

The bag body 11 was accommodated in the accommodation vessel 3, and 50 ml of umbilical cord blood using a heparin solution as an anti-coagulation agent was passed therethrough at a flow rate of 5 ml/min. whereby leukocytes derived from hematopoietic stem cells and/or hematopoietic precursor cells were captured in the filter material 12 in the inside of the bag body 11. Erythrocytes and platelets were passed through the bag body 11 and recovered in the erythrocyte-recovery bag 53. The yield of erythrocytes recovered in the erythrocyte-recovery bag 53 was 85% and the yield of platelets therein was 81%. Then, after closing the 3-directional stopcock 56, removing the accommodation vessel and relieving the compression of the bag body, dextran solution was passed through the bag body 11 so that leukocytes derived from hematopoietic stem cells and/or hematopoietic precursor cells were recovered in the leukocyte-recovery bag 54.

The volume expansion ratio of the bag body 11 and the yield of leukocytes recovered in the leukocyte-recovery bag 54, as determined in the same manner as in Example 1, are shown in Table 1.

EXAMPLE 3

A similar experiment to Example 1 was done by using the filter set 10 shown in FIG. 4. The bag body 11 and the filter material 12 are same as in Example 1.

The ratio of enlargement (volume expansion ratio) of the bag body 11 due to opening the lid and the recovery of leukocytes recovered in the leukocyte-recovery bag 54 are shown in Table 1.

The volume expansion ratio is the ratio of the inner volume of the bag body 11 in which the compression of the filter material 12 was relieved by opening the lid versus the inner volume of the bag body 11 in which the filter material 12 was compressed by closing the lid. The leukocyte recovery ratio is the ratio of the number of leukocytes in the dextran solution recovered in the leukocyte-recovery bag 54 versus the number of leukocytes in the blood originally accommodated in the blood bag 51.

EXAMPLE 4

A similar experiment to Example 2 was carried out using the filter set 10 shown in FIG. 4. The bag body 11 and the filter material 12 are same as in Example 2.

The ratio of enlargement of the bag body 11 due to opening the lid and the recovery of leukocytes recovered in the leukocyte-recovery bag 54 are shown in Table 1.

TABLE 1

|  | Volume expansion ratio (fold) | Leukocyte recovery ratio (%) |
| --- | --- | --- |
| Example 1 | 1.00 | 42.6 |
|  | 1.51 | 78.2 |
| Example 2 | 1.01 | 41.5 |
|  | 1.46 | 76.5 |
| Example 3 | 1.00 | 49.6 |
|  | 1.48 | 83.2 |
| Example 4 | 1.00 | 41.5 |
|  | 1.51 | 80.6 |

EXAMPLE 5

The filter set 1 shown in FIG. 6 was used. The filter material 12 charged in the bag body 11 consists of a 3-layer nonwoven fabric (filtration area 12.6 cm$^2$) using polyethylene terephthalate fibers. The structure of the three layers in the bag body 11 compressed in the accommodation vessel 3 consists of a nonwoven fabric with a fiber diameter of 10 μm and a bulk density of 0.19 g/cm$^3$ in an upper layer as a first layer, a nonwoven fabric with a fiber diameter of 3.5 μm and a bulk density of 0.05 g/cm$^3$ in an interlayer as a second layer and a nonwoven fabric with a fiber diameter of 1.8 μm and a bulk density of 0.14 g/cm$^3$ in a sublayer as a third layer. The weight ratio thereof was 52:21:27, and the total thickness was 6.0 mm.

Figure 7:
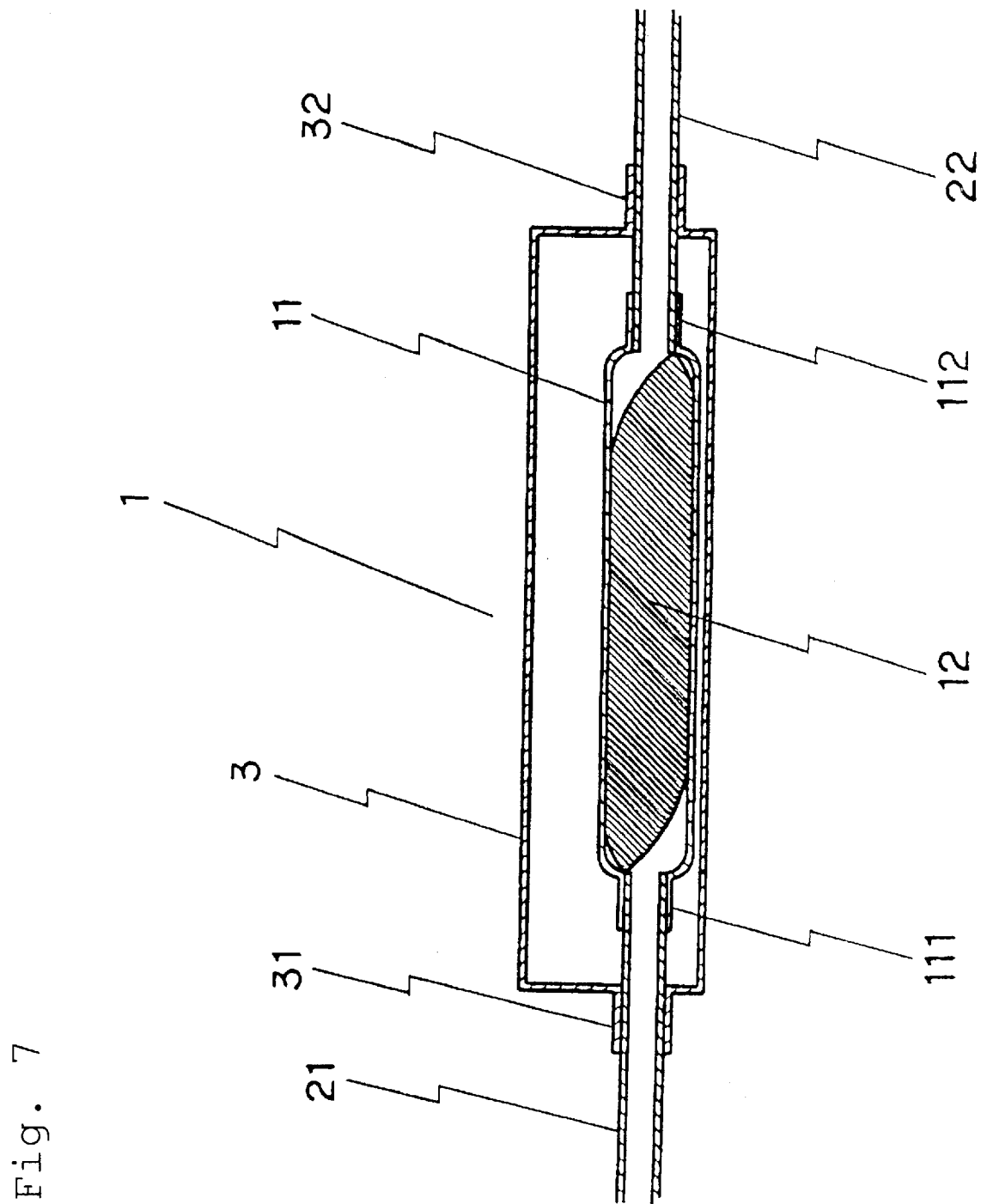
FIG. 7 is a longitudinal section of the bag body compressed by filling the blood filter set in FIG. 6 with compressed gas.

As shown in FIG. 7, the bag body 11 was compressed by injecting compressed air into the accommodation vessel 3 by use of a syringe, and 100 ml bovine blood containing ACD solution as an anti-coagulation agent was passed therethrough under a compressed condition at a flow rate of 5 ml/min. whereby leukocytes were captured in the inside of the bag body 11 while erythrocytes were passed through the bag body 11 and recovered in the erythrocyte-recovery bag 53 shown in FIG. 5.

The yield of erythrocytes recovered in the erythrocyte-recovering bag 53 was 90%, and the yield of platelets therein was 13%.

Figure 8:
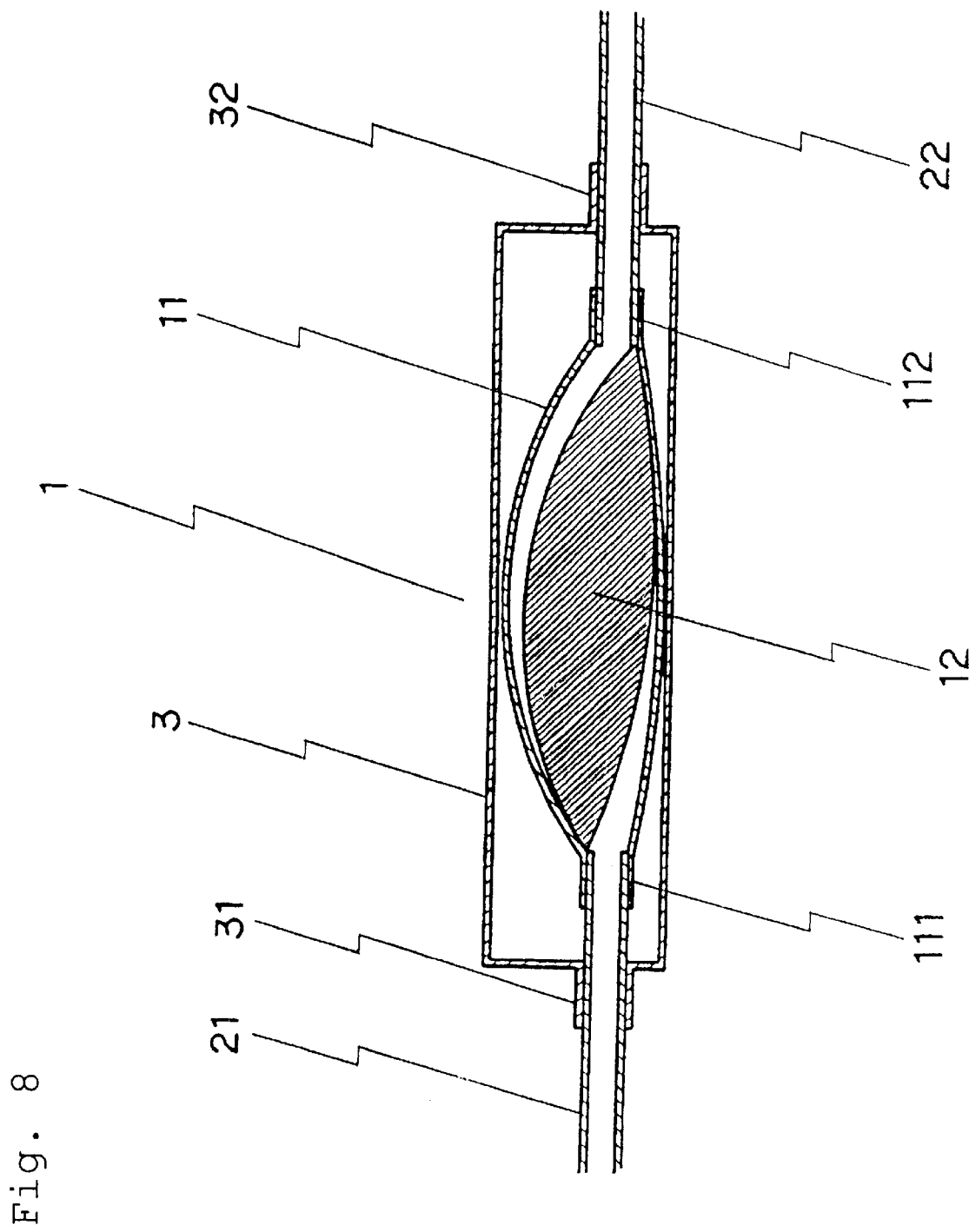
FIG. 8 is a longitudinal section showing the condition of the bag body whose compression was relieved by exhausting the compressed gas from the blood filter set shown in FIG. 6.

Then, the 3-directional stopcock 56 was closed and then the 2-directional stopcock 33 was opened to exhaust the compressed air from the accommodation vessel 3 so that as shown in FIG. 8, the bag body 11 was expanded due to relieved compression. Thereafter, the bag body 11 was filled with dextran solution to widen the spaces between the fibers. After shifting the direction of the 3-directional stopcock 56 to the leukocyte-recovering bag 54, 150 ml dextran solution was passed at a flow rate of 15 ml/min. and recovered in the leukocyte-recovery bag 54. The ratio of enlargement of the filter material 12 due to the relieved compression of the bag body 11 and the recovery of leukocytes recovered in the leukocyte-recovering bag 54 are shown in Table 2.

The volume expansion ratio is the ratio of the inner volume of the bag body 11 when the compression of the filter material 12 was relieved by exhausting the compressed air versus the inner volume of the bag body 11 in which the filter material 12 was compressed by filling the accommodation vessel 3 with the compressed air. The leukocyte recovery ratio is the ratio of the number of leukocytes in the dextran recovered in the leukocyte-recovery bag 54 versus the number of leukocytes in blood recovered in the blood bag 51.

TABLE 2

| Volume expansion ratio (fold) | 1.00 | 1.05 | 1.20 | 1.40 | 1.60 | 1.80 | 2.00 |
| --- | --- | --- | --- | --- | --- | --- | --- |
| Leukocyte recovery ratio (%) | 32.0 | 52.0 | 75.0 | 84.0 | 85.0 | 84.0 | 83.0 |

As is evident from Table 2, the yield of leukocyte increases with an increasing volume expansion ratio, but when the volume expansion ratio is 1.4 or more, the yield becomes nearly constant.

EXAMPLE 6

The filter set 1 shown in FIG. 6 was used. A nonwoven fabric with a fiber diameter of 10 μm and a nonwoven fabric with a fiber diameter of 1.8 μm were immersed in 0.25% 2-hydroxyethyl methacrylate/diethylaminoethyl methacrylate copolymer in ethanol to make a 2-layer laminate. A filter material 12 having a 2-layer structure consisting of said nonwoven fabric having a fiber diameter of 10 μm and a bulk density of 0.3 g/cm$^3$ as an upper layer (first layer) and said nonwoven fabric with a fiber diameter of 1.8 μm and a bulk density of 0.14 g/cm$^3$ as a sublayer (second layer) in a compressed condition (volume ratio 72.7:27.3) was accommodated in a bag body 11 (filtration area 12.6 cm$^2$).

The bag body 11 was compressed by injecting compressed air into the accommodation vessel 3 by use of a syringe, and 50 ml umbilical cord blood using a heparin solution as an anti-coagulation agent was passed therethrough at a flow rate of 5 ml/min. whereby leukocytes derived from hematopoietic stem cells and/or hematopoietic precursor cells were captured in the filter material 12 in the inside of the bag body 11.

Erythrocytes and platelets were passed through the bag body 11 and recovered in the erythrocyte-recovery bag 53. The yield of erythrocytes recovered in the erythrocyte-recovery bag 53 was 87% and the yield of platelets therein was 91%. Then, the 3-directional stopcock 56 was closed and the 2-directional stopcock 33 was opened to exhaust the compressed air thus relieving the compressed condition of the bag body 11. Dextran solution was passed into the bag body 11 so that leukocytes derived from hematopoietic stem cells and/or hematopoietic precursor cells were recovered in the leukocyte-recovery bag 54.

The volume expansion ratio of the bag body 11 and the yield of leukocytes recovered in the leukocyte-recovery bag 54, as determined in the same manner as in Example 1, are shown in Table 3.

TABLE 3

| Volume expansion ratio (fold) | 1.00 | 1.05 | 1.20 | 1.40 | 1.60 | 1.80 | 2.00 |
|---|---|---|---|---|---|---|---|
| Leukocyte recovery ratio (%) | 41.0 | 48.0 | 78.0 | 85.0 | 87.0 | 87.0 | 85.0 |

As is evident from Table 3, the yield of leukocytes increases with an increasing volume expansion ratio, but when the volume expansion ratio is 1.4 or more, the yield becomes nearly constant.

Effects of the Invention

As is evident from the foregoing description, blood components having adhered to the filter material can be efficiently recovered by the blood filter set of the present invention. Further, the time required for passing the washing solution can be reduced. The filter set of the present invention can relieve the compression of the filter material in a simple operation.

Explanation of the Reference Numerals
1,10 . . . filter set
11 . . . bag body
12 . . . filter material
111 . . . blood flow inlet
112 . . . blood flow outlet
21,22 . . . tube
3,4 . . . accommodation vessel
31,32 . . . bag body-removing port
33 . . . 2-directional stopcock
41 . . . lid
411 . . . arm
42 . . . vessel body
421 . . . protuberance
43 . . . groove
50 . . . blood components collecting apparatus
51 . . . blood bag
52 . . . washing solution bag
53 . . . erythrocyte-recovery bag
54 . . . leukocyte-recovery bag
55,56 . . . 3-directional stopcock
61 . . . ruptured portion
62 . . . perforation
63 . . . grasping portion

What is claimed is:

1. A blood filter set comprising a bag body having a blood flow inlet and a blood flow outlet and charged with a filter material, and an accommodation vessel for accommodating and compressing said bag body and filter material, said filter material having a bulk density of 0.05 to 0.05 g/cm$^3$ when compressed in said accommodating vessel and comprising an agglomerate of fibers, the fibers each having a diameter of 0.1 to 40 µm.

2. The blood filter set of claim 1, wherein the accommodation vessel is for accommodating said bag body which is freely removable therefrom and for accommodating said bag body and filter material in a compressed condition at the time of accommodation.

3. The blood filter set of claim 1, wherein the accommodation vessel has a lid which can be opened and closed.

4. The blood filter set of claim 1, wherein said accommodation vessel includes means for introducing a compressed gas thereinto.

5. The blood filter set of claim 1, wherein the bag body comprises a flexible sheet.

6. The blood filter set of claim 1, wherein the accommodation vessel is rigid.

7. The blood filter set of claim 1, wherein the accommodation vessel is a flexible tubular body.

8. A blood filter set comprising a bag body having a blood flow inlet and a blood flow outlet, said bag body comprising a flexible sheet charged inside with a filter material comprising an agglomerate of fibers, and a rigid accommodation vessel for accommodating said bag body which is freely removable therefrom and for accommodating said bag body in a compressed condition at the time of accommodation.

9. A blood filter set comprising a bag body having a blood flow inlet and a blood flow outlet, said bag body comprising a flexible sheet charged inside with a filter material comprising an agglomerate of fibers, and a rigid accommodation vessel for accommodating said bag body, wherein said accommodation vessel includes means for introducing compressed gas thereinto.

10. A blood filter set comprising a bag body having a blood flow inlet and a blood flow outlet and being charged with a filter material comprising an agglomerate of fibers, and a flexible tube body accommodating the bag body in a compressed condition in a thickness direction, wherein said body can be removed from said tube body.

11. The blood filter set of claim 10, wherein the tube body is a heat-shrunk tube.

12. The blood filter set of claim 10, wherein the tube is provided with a perforation along the length thereof to enable the tube to be ruptured.

13. The blood filter set of claim 10, wherein the tube body possesses a similar length to that of the bag body and a smaller volume than that of the bag body prior to compression of the bag body.

14. The blood filter set of claim 10, wherein the tube body is provided at at least one end thereof with a rib along an edge of the tube for grasping and removing the tube body from the bag body.

15. A method of recovering blood components comprising accommodating a bag body into an accommodation vessel, said bag body having a blood flow inlet and a blood flow outlet and having a filter material charged therein, compressing said bag body by said accommodation vessel, passing blood through said bag body in a condition compressed by said accommodation vessel to cause blood components to adhere the filter material, removing the bag body from said accommodation vessel and expanding said bag body, passing a washing solution through the inside of said bag body in an expanded condition so as to wash off the blood components adhered to said filter material, and recovering the blood components.

16. The method of claim 15, wherein the bag body comprises a flexible sheet.

17. The method of claim 15, wherein the accommodation vessel is rigid.

18. The method of claim 15, wherein the filter material is a fiber.

19. The method of claim 15, wherein the blood component is a leukocyte.

20. A method of recovering blood components comprising providing a rigid accommodation vessel and a bag body contained therein, filling said bag body with compressed gas to compress said bag body, said bag body having a blood flow inlet and a blood flow outlet, and comprising a flexible sheet charged inside with a filter material, passing blood through said bag body to cause blood components to adhere to the filter material, exhausting the compressed gas to relieve the compression condition of said bag body, passing a washing solution through the inside of said bag body so as to wash off the blood components adhered to said filter material, and recovering blood components.

21. The method of recovering blood components of claim 20, comprising the further step of evacuating the inside of said accommodation vessel to expand said bag body after the compressed gas is exhausted.

22. A method of recovering blood components comprising providing a bag body accommodated in a flexible tubular body in a compressed condition in a thickness direction, passing blood through said bag body, said bag body having a blood flow inlet and a blood flow outlet, and comprising a flexible sheet charged therein with a filter material, removing the bag body from the flexible tubular body to relieve the compression of the bag body, passing a washing solution through the inside of said bag body so as to wash off the blood components adhered to the filter material, and recovering the blood components.

* * * * *

UNITED STATES PATENT AND TRADEMARK OFFICE
CERTIFICATE OF CORRECTION

PATENT NO. : 6,129,853
DATED : October 10, 2000
INVENTOR(S) : Norihisa SASAYAMA et al.

It is certified that error appears in the above-indentified patent and that said Letters Patent is hereby corrected as shown below:

Column 14, line 3, "bulk density of 0.05 to 0.05 $g/cm^3$"

should read --bulk density of 0.05 to 0.50 $g/cm^3$--

Signed and Sealed this

Twenty-fourth Day of April, 2001

Attest:

NICHOLAS P. GODICI

Attesting Officer    Acting Director of the United States Patent and Trademark Office